United States Patent [19]

Nessi et al.

[11] Patent Number: 4,530,366
[45] Date of Patent: Jul. 23, 1985

[54] ELECTRONIC INSTRUMENT FOR THE CONTROL AND TREATMENT OF INFERTILITY IN WOMEN

[75] Inventors: Pierre Nessi, Geneva; Jacques Crausaz, Fribourg, both of Switzerland

[73] Assignee: Ares N.V. Amsterdam NL, Swiss Branch, Geneva, Switzerland

[21] Appl. No.: 443,889

[22] Filed: Nov. 23, 1982

[30] Foreign Application Priority Data

Dec. 1, 1981 [CH] Switzerland .......................... 7692/81

[51] Int. Cl.³ .............................................. A61B 5/00
[52] U.S. Cl. ..................................... 128/736; 128/738
[58] Field of Search ................................ 128/736, 738

[56] References Cited

U.S. PATENT DOCUMENTS

| 4,031,365 | 6/1977 | Raggioti et al. ............. | 128/736 X |
| 4,151,831 | 5/1979 | Lester ............................ | 128/736 |
| 4,367,527 | 1/1983 | Des Jacques ................ | 128/738 X |
| 4,396,020 | 8/1983 | Wolff et al. .................... | 128/738 |

FOREIGN PATENT DOCUMENTS

| 0147046 | 3/1981 | Fed. Rep. of Germany ...... | 128/736 |
| 0110927 | 8/1980 | Japan ................................. | 128/736 |
| 0110928 | 8/1980 | Japan ................................. | 128/736 |
| 2045480 | 10/1980 | United Kingdom . | |

Primary Examiner—Lee S. Cohen
Assistant Examiner—Angela D. Sykes
Attorney, Agent, or Firm—Cushman, Darby and Cushman

[57] ABSTRACT

A micro-computer-based instrument for characterizing a woman's menstrual cycle by measuring her temperature (BBT) each day and storing and analyzing those temperatures. The instrument defines, with user interaction, a time window each day during which it will accept a temperature measurement within a predetermined acceptable temperature range taken with the aid of a thermistor temperature probe than can be placed under the woman's tongue. The analysis carried out on the collected temperature data includes comparing, from the eighth day of a cycle, two average temperatures: $M_F$ (average of a presumed follicular phase) and $M_L$ (average of a presumed luteal phase). Comparison continues until the difference between $M_L$ and $M_F$ exceeds a predetermined level thereby defining a second phase of the cycle indicating that ovulation has occured. After characterizing the cycle, the instrument indicates the most appropriate days for hormone treatment, blood tests and physician visits so that fertility treatment can be optimized.

2 Claims, 1 Drawing Figure

ELECTRONIC INSTRUMENT FOR THE CONTROL AND TREATMENT OF INFERTILITY IN WOMEN

BACKGROUND OF THE INVENTION

This invention relates to an electronic instrument for measuring and analyzing a woman's basal bodily temperature (BBT) in connection with the treatment of infertility.

A normal menstrual cycle of a fertile woman is characterized by basal body temperature (BBT) curve that is biphasic, i.e., there is a rise in temperature a few hours after ovulation, a rise which generally occurs at about the middle of the menstrual cycle.

AT the present time, the BBT curve is obtained by manually measuring the woman's body temperature using a conventional thermometer every morning upon rising. The temperatures are manually plotted on a graph.

In cases of infertility the BBT curve is frequently abnormal. For this reason a gynecologist usually begins the investigation of an infertile patient by analyzing 2 or 3 cycles of the BBT.

In a certain number of cases of infertility, the BBT curve is not biphasic but monophasic or irregular; this leads us to suppose that ovulation is not occurring, or is occurring only intermittently. Faced with this situation, as in a certain number of others, the treatment adopted by the gynecologist includes hormone replacement therapy with the object of initiating a normal menstrual cycle in the patient, which would be characterized by a biphasic BBT curve.

To achieve a certain efficacy, the hormone replacement therapy must be given on certain precisely determined days throughout the patient's cycle. The intervals between treatment days, and also the interval between treatment and the observation of its results, must also fall on precisely determined dates.

SUMMARY OF THE INVENTION

Therefore, there is provided a micro-processor based electronic instrument for analyzing the BBT cycle and determining the appropriate times for hormone replacement, blood tests, physician observation, etc. The instrument includes a thermistor probe 11, a temperature input circuit 54, a clock 41, an RAM memory 53 a piezo-electric vibrator alarm 7, a continuous means for analysis of the BBT curve of temperatures and an LCD display 31 for providing analysis results to the user.

The instrument also includes means for prohibiting the acceptance of more than one temperature each day within a morning time window, and its acceptance only if the measured temperature falls between 35.0° C. and 37.5° C., and a system for replacing a missing temperature, or too high a temperature (such as might occur if the patient is running a fever), with the average temperature for the two days adjacent to it.

The instrument also includes a system enabling the comparison, from the 8th day of the cycle, of two average temperatures: $M_F$ (average of the presumed follicular phase—days 4 and 5) and $M_L$ (average of the presumed luteal phase—days 6, 7 and 8); the first 3 days are not taken into account. This comparing mechanism continues until $D = M_L - M_F$ exceeds a predetermined difference. When this predetermined difference is reached, it is presumed that the cycle is in its second phase, implying that ovulation has occurred; the antepenultimate day of the cycle is then considered as the Estimated Time of Ovulation—supposed (ETOs).

The instrument allows the patient suffering from infertility, and needing hormone replacement therapy, and the gynecologist, to know via the display (LCD), once the day for beginning treatment is fixed, the days for taking hormones, the days for blood-tests the day(s) for visiting the doctor, and the days forecast for maximum fertility.

The present invention provides an instrument capable of measuring the basal bodily temperature (BBT) automatically. The apparatus stores each new daily temperature on up to 200 occasions (about 3 complete menstrual cycles). In addition, the instrument analyzes the BBT curve in such a way as to detect a rise in temperature indicative of ovulation. At the end of a menstrual cycle—entered manually when the next menstrual period starts—the calculator analyzes the monthly BBT curve as a whole and fixes, with the help of a mathematical algorithm, referred to herein as algorithm no. 2, an ovulation day which corroborates or refutes the day of ovulation defined at the beginning of the daily temperature record. Then, in cases in which ovulation is known and confirmed, the instrument calculates and displays all individual temperatures, the length of the cycle, the estimated day of ovulation and the lengths of the post- and pre-menstrual phases. All these data are stored in the computers and are used for forecasts of the following cycles. Finally, when used in a mode T (hormonal treatment intended to restart a normal menstrual cycle), the apparatus displays, from the first day of treatment (fixed by the gynecologist) the days when the hormone has to be taken and the days fixed for a visit to the doctor for observation and/or blood tests.

The present invention thus provides electronic equipment for measuring the BBT, including an NTC probe (thermistor) to obtain the temperature, a temperature input circuit and a circuit to transform the measured temperature into digital data bits, a microprocessor for storage and processing of the information, and an LCD display for displaying the results of analysis. The instrument also has a clock which allows the day and the hour to be displayed at any moment, and authorizes only one measurement of BBT per day within a morning window predetermined by the patient. In the BBT mode the instrument also defines a temperature window for the acceptance of only temperatures within the range: 35.0° C.-37.5° C.

BRIEF DESCRIPTION OF THE DRAWINGS

The presently preferred embodiment of the invention will be further described with reference to a single figure, wherein.

DETAILED DESCRIPTION OF THE PREFERRED EMBODIMENT

Figure 1:
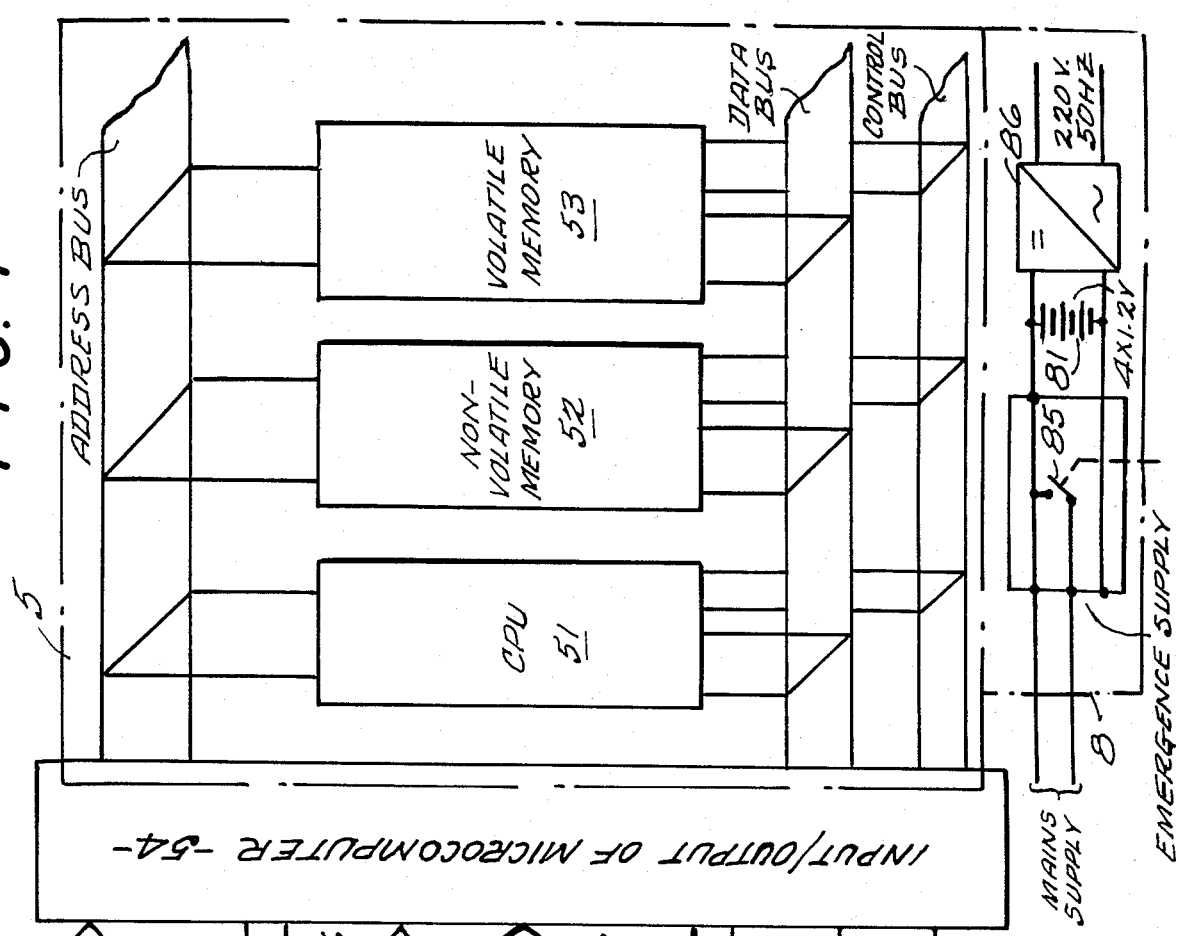
FIG. 1 is a block diagram of the electronic instrument according to the present invention.
Figure 1:
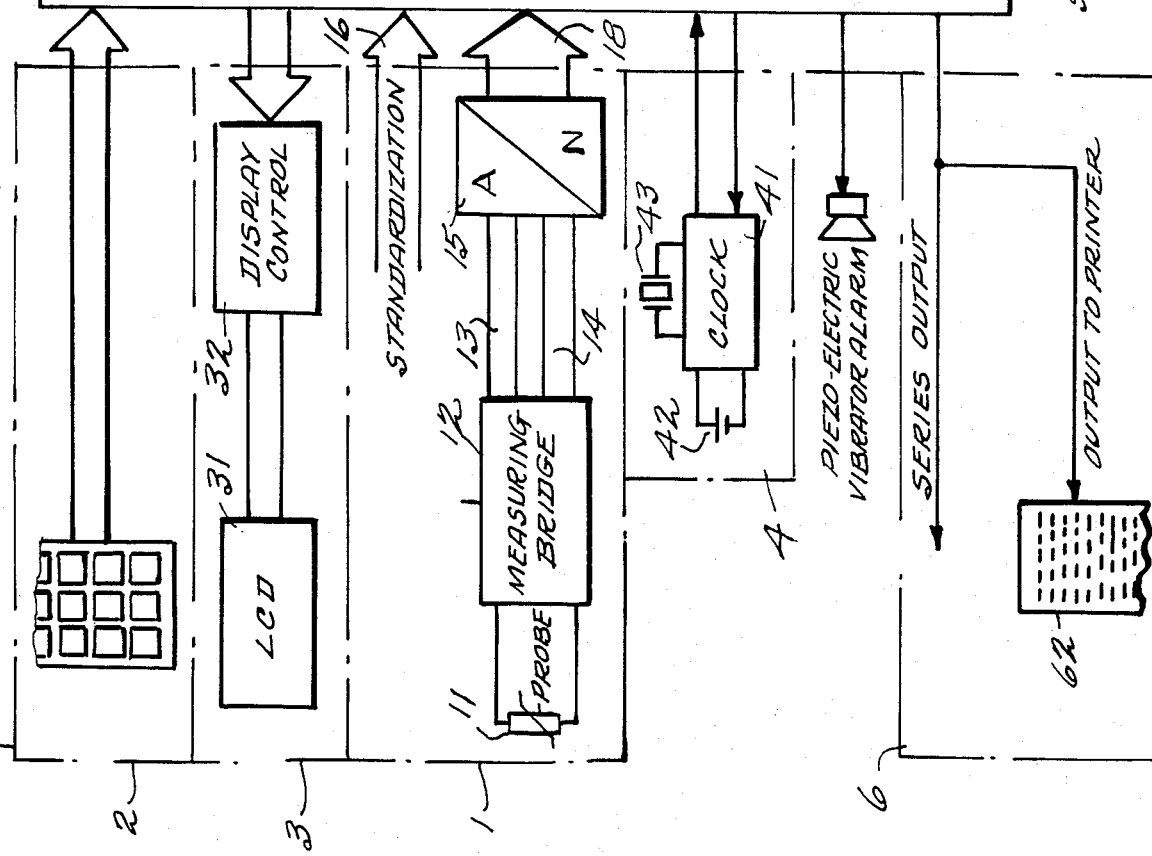

The operation and function of the instrument will be described first. Following that description, the hardware will be described with reference to FIG. 1.

To measure the BBT the apparatus is attached to an NTC probe, the tip of which is placed under the patient's tongue; the method of use is as follows:

(i) The beginning of the first cycle is indicated on the equipment by pressing code AAA (mode BBT) on the push-buttons of a keyboard data entry device. This operation effects a general reset and the display indicates that this day is day 1 of the cycle. This operation, carried out on the first day upon waking, fixes the "ideal" time for the daily measurement. Starting from this point, the instrument itself fixes a daily window of 4 hours (2 hours each side of the point) for the acceptance of a temperature reading. From day 2 up to the end of the cycle a sound signal occurring at the exact time of the point indicates to the patient that she has to take a reading.

(ii) The NTC probe is placed in the mouth, under the tongue. As soon as the temperature of the probe reaches a fixed threshold, the instrument operates automatically and measures the BBT in a similar way to that of a mercury thermometer (maximum thermometer). When the temperature is accepted by the instrument, a sound signal indicates to the patient that measurement is complete; the instrument "goes to sleep again" automatically.

(iii) The temperatures of the first 3 days of the cycle are stored, but are not taken into account in the analysis of the curve. The calculator then accepts 5 more daily temperatures (days 4-5-6-7-8) before beginning the analysis of the curve using an algorithm referred to herein as algorithm no. 1. Once the temperature for day 8 is stored, the instrument calculates:

(1) $M_F$=arithmetical average of days 4 and 5
(2) $M_L$=arithmetical average of days 6-7 and 8
(3) $D=M_F-M_L$ If $D>0.3$, the first of the 3 days forming the average $M_L$ (here, day 6) is taken to be the day of ovulation (0). If, on the other hand, $D<0.3$, the calculator waits for the next temperature and re-calculates D from the average ($M_L$) of the last 3 days of the cycle that have been entered (now 7-8-9) and that ($M_F$) of all the preceding days (now 4-5-6) and so on until D is greater than 0.3° C.

(iv) When $D>0.3$, the antepenultimate day of the cycle is taken as the day of ovulation (day 0). Once day 0 is found, algorithm no. 2 is used for the following days: the average of the follicular (post-menstrual) phase, taken as $M_F$, does not change; on the other hand the average of the luteal phase (pre-menstrual phase), taken as $M_L$, is then calculated using all the days of the cycle from day 0, and thus changes with every newly entered temperature. Day 0 is confirmed as the day of ovulation if $D=M_L-M_F$ remains above or equal to 0.2° C. for at least 3 days (that is to say 0+6). If D again becomes less than 0.2° C. before day 0+6, algorithm no. 1 is used again, and the search for an ovulation day begins again.

(v) If a day is missed, or if the temperature of one day is over 37.5° C. (fever), the temperature for that day is replaced by the average of the day preceding it and the day immediately following it.

(vi) Using algorithms no. 1 and no. 2, it is possible to reach the end of the cycle without observing or fixing a day of ovulation. In such a situation, and only at the end of the cycle, the instrument uses an algorithm referred to herein as algorithm no. 3 which, having available all the temperatures of the cycle, proceeds to seek a biphasic or monophasic cycle with the help of the following mathematical scheme:

(1) The cycle is arbitrarily divided into 4 equal parts, I, II, III, and IV, and the average temperature of each of these 4 parts is calculated: $M_I$, $M_{II}$, $M_{III}$ and $M_{IV}$. These 4 averages are then compared with the overall average of the cycle M. There are then 16 possible mathematical combinations represented by the following table:

| $M_I$ | $M_{II}$ | $M_{III}$ | $M_{IV}$ | No. | Comments |
| --- | --- | --- | --- | --- | --- |
| + | + | + | + | 1 | impossible |
| + | + | + | − | 2 | irregular or monophasic |
| + | + | − | + | 3 | biphasic to be confirmed ($M_{IV}$) |
| + | + | − | − | 4 | irregular/monophasic |
| + | − | + | − | 5 | biphasic to be confirmed ($M_{III}$) |
| + | − | − | + | 6 | biphasic to be confirmed ($M_{IV}$) |
| + | − | − | − | 7 | irregular/monophasic |
| + | − | + | + | 8 | biphasic |
| − | + | + | + | 9 | biphasic |
| − | − | + | + | 10 | biphasic |
| − | + | + | − | 11 | biphasic |
| − | − | + | − | 12 | biphasic to be confirmed ($M_{III}$) |
| − | + | − | + | 13 | biphasic to be confirmed ($M_{IV}$) |
| − | − | − | + | 14 | biphasic |
| − | + | − | − | 15 | irregular/monphasic |
| − | − | − | − | 16 | impossible |

+ = $M_{I, II, III}$ or $_{IV}$ above M
− = $M_{I, II, III}$ or $_{IV}$ below M

The extreme situations (1 and 16) are impossible. Situations 2-4-7-15 are very probably characteristic of irregular (monophasic) curves. Situations 3-5-6-12-13 are perhaps biphasic but need a confirming algorithm. Finally, situations 8-9-10-11-14 are very probably biphasic.

(2) In cases where we are faced with an irregular or monophasic curve (2-4-7-15) this is shown in the display for the attention of the gynecologist; a new cycle can then be started without losing information about the preceding cycle.

(3) In cases in which we are confronted with a biphasic curve (8-9-10-11-14), algorithm no. 4 is used to find the ovulation day. Moving along the cycle, we find the first daily temperature above the general average, M, of the cycle: day $P_1$. Then, starting from day $P_1$, we find the next 5 days, $P_1$ is not considered as the day of ovulation, 0, and the process of seeking begins again. If, on the other hand, $D=P_2-P_1$ is more than 5 days or if $P_2$ coincides with the antepenultimate, the penultimate or the last day of the cycle, $P_1$ is considered as the day of ovulation.

(4) In cases in which we are faced with a biphasic curve to be confirmed (3-5-6-12-13), algorithm no. 4 is used also. When the day of ovulation 0 is found, a confirming algorithm 5 checks whether the day of ovulation found is situated in a quadrant which is "numbered" (+) with respect to M, and whether this quadrant is $M_{III}$ or $M_{IV}$. If both of these conditions are not satisfied, day 0 is rejected and the phrase "irregular curve" is displayed.

(vii) If the processor has observed a day 0 when the results are fed in, it stores this information in its memory. At the end of the cycle, it looks again for the day of ovulation, using algorithms 3 and 4, described under (vi). If this day 0 corresponds with the day of ovulation (+or−2 days) found with the help of algorithms 1 and 2, then day 0 is definitely confirmed. In the contrary case, the confirming algorithm no. 5 is used again to accept or reject the ovulation day 0 (of point (4) paragraph (vi)).

(viii) If ovulation is definitively confirmed, it is possible to show on the display: the length of the cycle, day 0 and take lengths of the follicular and luteal phases. All these values are stored in the memory for the purpose of forecasting future cycles.

(ix) Where the curve is irregular or monophasic, the gynecologist can try to establish a biphasic cycle by giving his patient hormonal treatment. Given that hormonal treatment generally follows a classic scheme, the instrument will indicate to the patient when she has to take her hormonal treatment and when she has to go to the doctor's for examination or blood test.

The instrument can also indicate, to a couple wishing to conceive, which is the period of maximum fertility. This forecast uses the information stored during previous cycles. The instrument also has a normalized "series" output which enables the temperatures of the cycle to be transferred to a more powerful computer, and thus a more complete analysis of the curve to be carried out; or it allows the temperatures to be printed on a pocket printer and the monthly curve to be printed on it in summary.

The instrument can be used as a watch and a digital calendar, and as a medical thermometer. Access to information is possible at any moment by using special functions which do not alter the functioning of the instrument as an electronic calculator used for the treatment of infertility in women. It follows from the above that the equipment can also be used in the field of family planning.

Referring now to FIG. 1 (the sole FIGURE) there is shown a block diagram of the electronic instrument according to the present invention. The electronic instrument specially developed for the control and treatment of infertility in women features a micro computer integrated on a single silicon chip. The instrument includes the following main elements and/or functions.

MEASUREMENT

A measuring probe 11 is provided for sensing the patient's temperature. It comprises a resistor having a negative temperature coefficient (NTC). The resistor is encapsulated in a protective material that can be safely taken into the mouth. The probe resistance forms an element of a Wheatstone measuring bridge 12. A difference in potential 14 created by an imbalance of the bridge across a bridge diagonal is converted to a binary number by the analog-numerical converter 15 preferably of the type having a double gradient.

This integrates, for a constant length of time, the bridge diagonal potential difference 14 and then feeds its integrator with a potential in proportion 13 to the feed potential of the bridge. As a result a binary number 14 resulting from analog to numerical conversion depends only on the resistances of the bridge. The resistances of the bridge are chosen in such a way that standardization only of the minimum point of the measuring range is necessary. This standardization is carried out digitally with the help of a binary input (16), the bridge having no variable resistance.

Specifications:
measuring range 35° C. to 40° C.
resolution +0.05° C.
absolute precision +0.1° C.

CONTROL

A numerical keyboard 2 including twelve keys provides a means for entering data and for causing the equipment to operate in a selected one of its different modes of operation. The entry of data or instructions through the keyboard is carried out by the keys being pressed in sequence. Each command is represented by a code which is displayed on a display screen.

DISPLAY

The instrument includes an alpha-numerical display (31) such as, for example a liquid crystal display (LCD) connected with the micro-computer via a display control (32) for carrying out demultiplexing. It can display very clearly:
input or keyboard selection
the measured temperature
the readings of a clock
the results of analyses and the requisite treatment

CLOCK

The instrument includes an autonomous clock circuit (41) capable, from a quartz crystal (43) of providing the processor or user, at any moment, with the complete data and time. When the instrument is functioning normally, the clock is used mainly for dating the daily temperature readings which are accepted only within a four-hour window. The clock also enables the patient to be told:
the time of the daily temperature reading, by a ring on a piezo-electric vibrator
the daily actions to be carried out in the case of treatment Clock 41 is powered by a battery 42 to ensure that the clock functions without interruption.

MICRO-COMPUTER

As previously stated, the instrument features a micro-computer. The micro-computer includes the following elements:
central processing unit 51 providing for the running of the system
non-volatile memory 52 such as a PROM or a ROM containing the program governing the functioning of the equipment and of the treatment program as a whole
volatile memory 53 such as a RAM Memory 53 is preferably selected to be a CMOS device, the supply voltage of which is kept constant by the batteries of the supply system. This memory allows the recording of the requisite treatment for infertility and of all intermediate results generated from preceding analyses
communication units such as, for example, an input-/output (I/O) device 54 enabling all the peripheral elements to properly interface with other micro-computer elements.

SERIES OUTPUT

Circuitry enables the user to transfer all the data contained in the memory both to other calculators for a normalized series output 61 and to a thermic mini-printer symbolized by a printed document 62 so as to obtain a "hard" copy of the results of analysis.

PIEZO-ELECTRIC VIBRATOR

The instrument includes a piezo-electric vibrator 92 controlled by the micro-computer, enabling the important events in the functioning of the instrument to be acoustically signalled. These events might include but not be limited to the following:
time of temperature reading
end of temperature reading
important event for treatment

ELECTRICAL SUPPLY

The electrical supply to the equipment is provided by a filtered rectifier circuit 86 connected to a power supply such as commercial power provided by a utility company. If the means should fail, if it accidentally disconnected, or the device has to be moved, the main functions (volatile memory and clock) are maintained by a supply from the batteries 81 which are automatically charged by the connection to the mains. If there is no mains supply, only a certain number of important circuits are supplied; the others are disconnected by means of a trip 85.

While the invention has been described in connection with what is presently considered to be the most practical and preferred embodiments, it is to be understood that the invention is not to be limited to the disclosed embodiments but on the contrary, is intended to cover various modifications and equivalent arrangements included within the spirit and scope of the appended claims which scope is to be accorded the broadest interpretation so as to encompass all such modifications and equivalent structures.

What is claimed is:

1. A method for characterizing a woman's menstrual cycle for aiding in the treatment of infertility comprising the steps of:

measuring and storing the woman's temperature on each of at least the first eight days of a menstrual cycle;

disregarding the temperatures taken on days 1 to 3;

calculating the mean value $M_F$ of the temperatures taken on days 4 and 5;

calculating the mean value $M_L$ of the temperatures taken on days 6, 7 and 8;

determining the difference $D = M_F - M_L$;

if D is greater than 0.3° C., defining the first of the three days forming the average $M_L$ as the day of ovulation;

if D is less than 0.3° C., waiting for the next temperature and recalculating D from the mean $M_L$ of the last three days of the cycle that have been entered and an $M_F$ of all days preceding the last three days used for the calculation of $M_L$ and so on until D is greater than 0.3° C.;

when D is greater than 0.3° C., defining the antepenultimate day of the cycle as the day of ovulation;

once the day of ovulation is determined, using a first predetermined algorithm for processing temperature measurements taken on days following the day defined as the day of ovulation, this algorithm being characterized as follows: the average of the follicular (post-menstrual) phase, taken as $M_F$ does not change, however the average of the luteal phase (pre-menstrual phase) taken as $M_L$ is calculated, using all of the days of the cycle from the day defined as the ovulation day thereby changing with each newly entered temperature, the ovulation day being confirmed as the day of ovulation if $D = M_L - M_F$ remains above or equal to 0.2° C. for at least three days; and if D again becomes less than 0.2° C. before the sixth day following the day defined as the day of ovulation, using said first algorithm or redefining the day of ovulation; and in the event that the end of the cycle is reached without observing or defining a day of ovulation, utilizing a second algorithm to determine whether there exists a biphasic or monophasic cycle according to the following mathematical scheme: the cycle is arbitrarily divided into four equal parts I, II, III, and IV and the average temperature of each of these four parts is calculated: $M_I$, $M_{II}$, $M_{III}$, and $M_{IV}$; these four average temperatures then being compared with the overall average M of the complete cycle to yield one of sixteen possible mathematical combinations as set forth in the following table:

| $M_I$ | $M_{II}$ | $M_{III}$ | $M_{IV}$ | No. | Comments |
|---|---|---|---|---|---|
| + | + | + | + | 1 | impossible |
| + | + | + | − | 2 | irregular or monophasic |
| + | + | − | + | 3 | biphasic to be confirmed ($M_{IV}$) |
| + | + | − | − | 4 | irregular/monophasic |
| + | − | + | − | 5 | biphasic to be confirmed ($M_{III}$) |
| + | − | − | + | 6 | biphasic to be confirmed ($M_{IV}$) |
| + | − | − | − | 7 | irregular/monophasic |
| + | − | + | + | 8 | biphasic |
| − | + | + | + | 9 | biphasic |
| − | − | + | + | 10 | biphasic |
| − | + | + | − | 11 | biphasic |
| − | − | + | − | 12 | biphasic to be confirmed ($M_{III}$) |
| − | + | − | + | 13 | biphasic to be confirmed ($M_{IV}$) |
| − | − | − | + | 14 | biphasic |
| − | + | − | − | 15 | irregular/monophasic |
| − | − | − | − | 16 | impossible |

+ = $M_{I, II, III}$ or $_{IV}$ above M
− = $M_{I, II, III}$ or $_{IV}$ below M;

in the event of an irregular or monophasic curve, providing an indication thereof; and in the event of a biphasic curve, utilizing a third algorithm to determine the ovulation day, said third algorithm comprising the steps of:

determining the first daily temperature above a general average M of temperatures over the complete cycle; defining this as a temperature occurring on day $P_1$;

starting from day $P_1$, determining the next temperature below M, this temperature being designated as occurring on day $P_2$;

if the different $D = P_2 - P_1$ is less than five days, considering $P_1$ as not being the day of ovulation and repeating the process; and if $D = P_2 - P_1$ is more than five days or if $P_2$ coincides with the antepenultimate day, the penultimate day or the last day of the cycle, considering $P_1$ as the day of ovulation; and indicating the determined day of ovulation.

2. A method according to claim 1 further including the steps of:

confirming a biphasic curve using said third algorithm; and using a confirming fourth algorithm to check whether the day of ovulation as determined is situated in a quadrant (+) with respect to M and whether this quadrant is $M_{III}$ or $M_{IV}$; and if both of these conditions are not satisfied, rejecting the day of ovulation and providing an indication of an irregular curve.

* * * * *